United States Patent [19]

Whitney et al.

[11] Patent Number: 4,634,431
[45] Date of Patent: Jan. 6, 1987

[54] SYRINGE INJECTOR

[76] Inventors: Douglass G. Whitney, 3800 State Bridge Rd., Alpharetta, Ga. 30201; J. Kell Martin, III, 2837 Ridge Wood Circle, Atlanta, Ga. 30327

[21] Appl. No.: 494,662

[22] Filed: May 16, 1983

Related U.S. Application Data

[60] Continuation-in-part of Ser. No. 248,512, Mar. 27, 1981, Pat. No. 4,405,318, which is a division of Ser. No. 1,091, Jan. 8, 1979, Pat. No. 4,273,122, which is a continuation-in-part of Ser. No. 741,528, Nov. 12, 1976, Pat. No. 4,150,762.

[51] Int. Cl.$^4$ ............................................. A61M 37/00
[52] U.S. Cl. ..................................... 604/155; 604/154; 604/224; 604/228; 222/333; 222/390; 128/DIG. 1
[58] Field of Search ................................ 604/154–155, 604/141, 146, 151, 152, 207–208, 224, 228; 128/DIG. 1, DIG. 12, DIG. 13; 222/333, 390

[56] References Cited

U.S. PATENT DOCUMENTS

| | | | |
|---|---|---|---|
| 951,160 | 3/1910 | Wainwright | 604/224 |
| 996,128 | 6/1911 | Payne et al. | 604/224 |
| 1,756,811 | 4/1930 | Brownsberger et al. | 222/390 |
| 2,052,296 | 8/1936 | Huntley | 222/390 |
| 2,187,168 | 1/1940 | McAssey | 604/224 |
| 4,475,666 | 10/1984 | Bilbrey et al. | 604/152 |

Primary Examiner—Stephen C. Pellegrino
Assistant Examiner—Gene B. Kartchner
Attorney, Agent, or Firm—B. J. Powell

[57] ABSTRACT

A syringe injector for injecting liquids into patients comprising a syringe barrel with a slidable piston therein and a driver slidably extending into the barrel bore from the open end thereof behind the piston, where the driver includes a power supply and drive means operated by the power supply to cause at least a portion of the driver to move relative to the barrel to engage and propel the piston toward the discharge opening in the syringe barrel.

2 Claims, 18 Drawing Figures

SYRINGE INJECTOR

CROSS-REFERENCE TO RELATED APPLICATIONS

This application is a continuation-in-part of our co-pending application Ser. No. 248,512, filed Mar. 27, 1981, now U.S. Pat. No. 4,405,318, which is a division application of our application Ser. No. 1,091, filed Jan. 8, 1979, now U.S. Pat. No. 4,273,122, which is a continuation-in-part of our application Ser. No. 741,528, filed Nov. 12, 1976, now U.S. Pat. No. 4,150,762.

BACKGROUND OF THE INVENTION

This invention relates generally to devices for dispensing or injecting a fluid at a controlled rate and more particularly to a device for use in the medical field to inject fluids into the body of a patient at controlled rate over a prescribed period of time.

It is desirable in the medical profession to inject fluids such as liquid medicaments into the body of the patient, whether human or animal, at a relatively slow rate over a prolonged period of time. Several varieties of medical treatments such as chemotherapy, pre-and post-surgery treatments for the prevention of blood clotting, various nutrient treatments, various antibiotic treatments and treatment of certain other diseases generally require low rates of injection over a long period of time. Such injections are generally made intravenously or subcutaneously into the patient. Some of these treatments generally require that the fluid be introduced relatively continuously over some period of time at some selected rate. Different treatments may require widely varying injection rates. Because of significant increase in the predetermined rate of injection during these continuous treatments must be accurately controlled to prevent serious injury to or fatality of the patient, the rate of injection must be frequently and closely monitored.

There are a number of liquid dispensing or injection devices presently known which attempt to dispense or inject a liquid into a patient at a continuous rate over an extended period of time. These prior art injection systems, however, suffer from a number of drawbacks.

One drawback of such prior art injection systems is that they have tended to be complex in construction and bulky in size. Another drawback of such prior art injection systems is that the injection rate was typically inaccurate and thus required frequent monitoring by trained hospital personnel. Yet another drawback to such systems is that the capital cost thereof is too high for the systems to be disposable. As a result, use of these prior art systems has been limited primarily to hospital settings and under conditions which severely encumber ambulation by the patient. This keeps the utilization costs of such systems high. Moreover, injection rate adjustments had to be made at the site of the patient rather than at the pharmacy where the medication is prepared, thereby increasing the likelihood of error in the delivered dosage rate.

SUMMARY OF THE INVENTION

These and other problems and disadvantages associated with the prior art are overcome by the invention disclosed herein by providing an injector system which can accurately inject fluids yet is simple in construction and operation. Further, the injector is sufficiently small to allow the patient to remain free to move about while the injector is in use so as to promote outpatient drug delivery. The injection rate is easily monitored and is safe beyond clinical requirements so as to allow use of the system in out-patient settings. The injection rate can be continuously varied over a prescribed injection rate range and the injection rate can be preset at the pharmacy where the medication is prepared to reduce the likelihood of error in the injection rate prescribed by the physician. The injector system permits the incorporation of the syringe barrel and piston from standard commercially available syringes with a self-propelled plunger to minimize system cost and allow for the system to be disposable.

The apparatus of the invention includes a syringe barrel defining a cylindrical bore therein opening onto one end thereof and a discharge opening in the other end thereof communicating with the bore with a piston slidably mounted in the bore in sealing engagement with said barrel for movement toward the discharge opening to force liquid in the bore out through the discharge opening. Both the syringe barrel and piston may be from a standard syringe.

A self-propelled driver is provided to fit into the barrel bore behind the piston with a power supply and drive means operated by the power supply to cause at least a portion of said driver to move axially of the syringe barrel to engage and propel the piston toward the discharge opening at a controlled rate. In some embodiments, the driver has a power unit which remains fixed to the syringe barrel within the bore and a plunger which is axially shifted over the power unit to move the piston. In other embodiments, the entire driver is received in and axially advanced along the bore to move the piston.

These and other features and advantages of the invention disclosed herein will become more apparent upon consideration of the following specification and accompanying drawings wherein like characters of reference designate corresponding parts throughout the several views and in which:

These figures and the following detailed description disclose specific embodiments of the invention; however, it is to be understood that the inventive concept is not limited thereto since it can be incorporated in other forms.

DETAILED DESCRIPTION OF ILLUSTRATIVE EMBODIMENTS

The injector 10 seen in FIGS. 1-5 incorporating the invention includes a syringe barrel 11 within which is slidably mounted a piston 12. A driver 14 is inserted into the barrel 11 behind the piston 12 and is self-propelled to force the piston along the syringe barrel to expel liquids from the barrel. The barrels and pistons from standard commercially available syringes may be utilized for the barrell 11 and piston 12 and are illustrated as such in the drawings.

Figures 1, 2, 3, 4, 5:
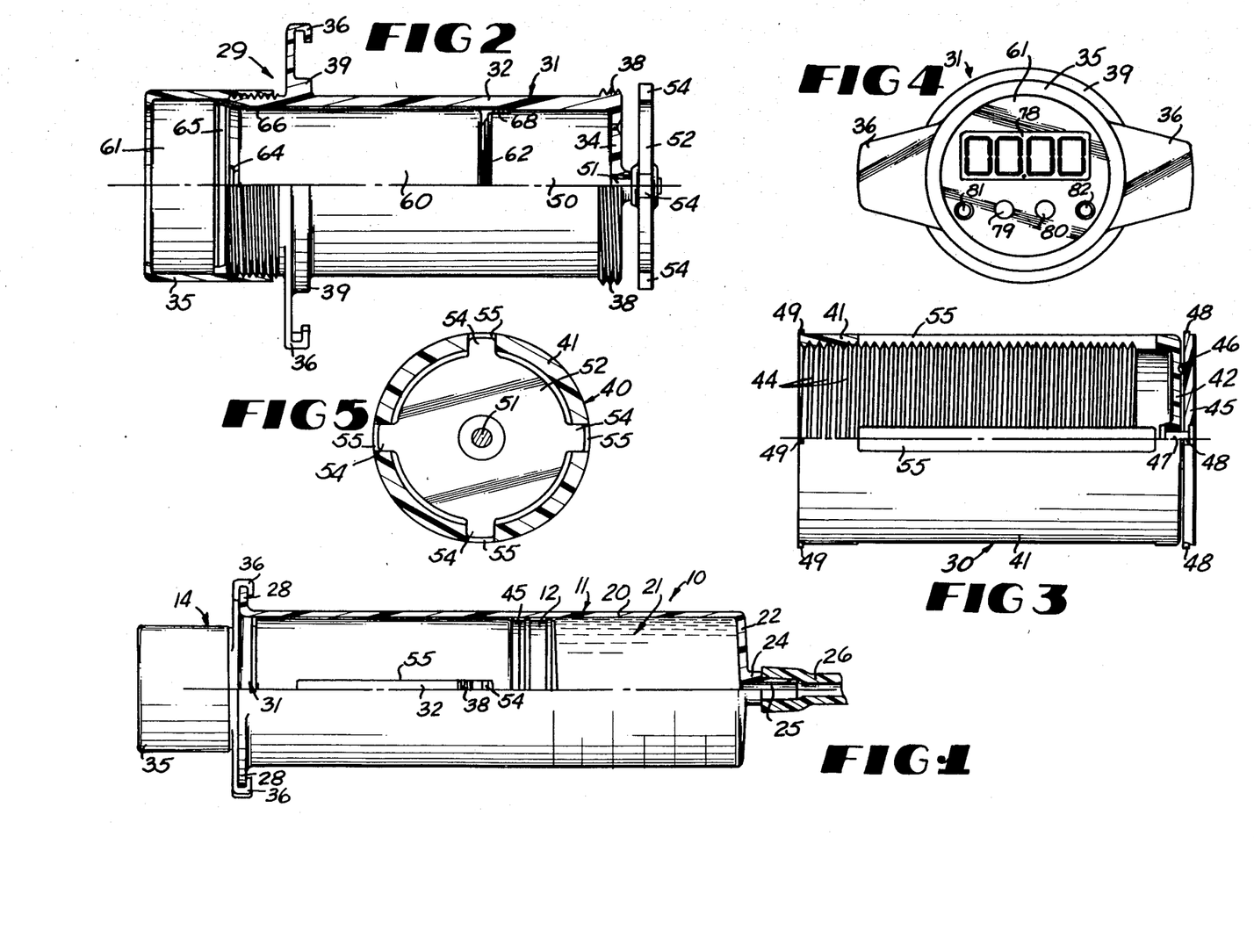
FIG. 1 is an elevational view shown partly in section of an injector embodying the invention.
FIG. 2 is an enlarged elevational view of the power unit of the driver of the invention shown partly in cross-section.
FIG. 3 is an enlarged elevational view of the plunger of the driver shown partly in cross-section.
FIG. 4 is a cap end view of the driver of the invention.
FIG. 5 is a cross-sectionanal view of the driver of the invention taken generally along line 5—5 in FIGS. 2 and 3.

The syringe barrel 11 is generally cylindrical in shape with a seamless annular side wall 20 defining a cylindrical bore 21 therethrough closed at one end of side wall 20 by an end wall 22 and opening onto the opposite end of side wall 20. A connecting tip 24 is provided on end wall 22 with a discharge opening 25 therethrough communicating with the end of central bore 21 so that liquids in bore 21 can be discharged out through the opening 25. The tip 24 is adapted to be connected to a piece of IV tubing 26 as seen in FIG. 1 usually equipped with an IV needle (not shown) so that the discharge opening 25 can be intravenously connected to a patient. That end of the side wall 20 opposite the end wall 22 is provided with a pair of opposed ears 28 as is common with standard syringe barrels.

The piston 12 may be a standard syringe piston and is provided with elastomeric sealing rings so that the piston 12 remains sealed to the barrel side wall 20 as the piston slides along the bore 21. Thus, it will be seen that the fluid in the bore 21 between the piston 12 and the end wall 22 is discharged through the opening 25 as the piston 12 is moved toward the end wall 22. It will be appreciated that the length of the syringe barrel is such that enough space is left in bore 21 behind the piston 12 for the driver 14 to be received therein when the maximum volume of fluid to be injected is confined in the bore 21 by piston 12.

The driver 14 includes a power unit 29 which threadedly receives a hollow plunger 30 thereover. The power unit 29 is held fixed in the syringe barrel 11 and rotates the plunger 29 to axially project the plunger 30 from over the power unit 29 and move piston 12 toward the discharge opening 25.

The power unit 29 includes an elongate cylindrical housing 31 best seen in FIG. 2 with an outside diameter a prescribed amount smaller than the bore 21 as will become more apparent. The housing 31 has an annular side wall 32 closed at its leading end by an end wall 34 to define a cavity therein opening onto the opposite end of the side wall 32. A cap member 35 threadedly engages the open end of side wall 32 to close the cavity in the housing. A pair of opposed locks 36 are mounted on the side wall 32 adjacent the cap member 35 and project outwardly therefrom. The locks 36 are constructed and arranged to selectively grip the ears 28 on the syringe barrel 11 and lock the power unit 29 onto the syringe barrel 11 with the leading end of the housing 31 projecting into the bore 21 in barrell 11 behind the piston 12 as seen in FIG. 1. A raised externally threaded section 38 is provided around the outside of the housing side wall 32 at its leading end. The threaded section 38 is relatively short as will become more apparent. The side wall 32 is provided with an annular locating section 39 immediately forward of the locks 36 to just fit in the end of bore 21 and keep the housing 31 coaxially located with respect to the bore 21.

The tubular plunger 30 best seen in FIG. 3 has an annular cylindrical side wall 41 closed at its leading end by an end wall 42. The outside diameter of the side wall 41 is such that the plunger 30 will be received in the bore 21 of the syringe barrel 11 in close tolerance clearance therewith. The inside of side wall 41 is provided with internal threads 44 along its length sized to be screwed onto the externally threaded section 38 of housing 31 so that the side wall 41 overlaps the side wall 32 on housing 31 as seen in FIG. 1. Thus, as the plunger 30 is rotated with respect to housing 31, the threads 38 and 44 shift the plunger axially of housing 31. A drive plate 45 is rotatably mounted on the outside of the end wall 42 on bearing 46 and shaft 47 to rotate about the longitudinal axis of the plunger 40. The leading end face on the drive plate 45 has an outside diameter substantially that of the piston 12 to engage the trailing end of piston 12 and move the piston toward the end wall 22 in barrell 11. Positioners 48 may be provided around the periphery of the plate 45 and/or around the leading end of side wall 41 to slide along the bore 21 and keep the leading end of the plunger 30 concentrically of the bore 21 while minimizing the sliding friction therebetween. Similar positioners 49 may be provided on the outside of the trailing open end of side wall 41 to keep the trailing end of the plunger 30 concentric of bore 21. It will thus be seen that when the locks 36 on poewr unit 29 engage the ears 28 on the barrel 11 as seen in FIG. 1, unscrewing the plunger 30 from over the housing 31 will move the drive plate 45 toward the discharge opening 25 in barrel 11 and force the fluid out of the discharge opening.

To rotate the plunger 30, a drive motor 50 best seen in FIG. 2 is fixedly mounted in the leading end of the cavity in the housing 31 with its drive shaft 51 rotatably extending through the end wall 34 in the housing. This locates the projecting end of the shaft 51 inside the plunger 30. The shaft 51 mounts a drive wheel 52 thereon just forward of the end wall 34 in housing 31. The main body of drive wheel 52 as seen in FIG. 5 has an outside diameter smaller than the inside diameter of the plunger side wall 41 and is provided with a plurality of circumferentially spaced lugs 54 which subtend a diameter larger than the inside diameter of the plunger side wall 41. The plunger side wall 41 is provided with a plurality of inwardly opening slots 55 therein which extend longitudinally of the plunger side wall 41 and are circumferentially spaced therearound so as to be registerable with the lugs 54 on drive wheel 52. Thus, it will be seen that the lugs 54 can slide longitudinally of slots 55 to maintain driving contact between the plunger 40 and drive motor 50 as the threads 38 and 44 shift plunger 30 axially of the housing 31. While drive motor 50 may be any of a variety of different types of motors, it is preferred that a stepping motor be used in order that the rotation of the drive shaft 51 be accurately controlled. It will be appreciated that the motor 50 rotates the drive wheel 52 in the direction to cause the plunger 30 to be unscrewed off of the housing 31.

A battery 60 as seen in FIG. 2 is slidably mounted in the cavity of housing 31 behind the motor 50 to power same. The inside diameter of the housing side wall 32 is sized so that battery 60 can be of a standard size. A controller 61 is mounted in the cap member 35 and serves to connect the battery 60 to the motor 50 to power same. Whie different connections may be used, the minus or negative terminal of the battery 60 is turned toward the motor 50 and is connected thereto through a conical coil spring 62 which also serves to resiliently position the battery as will become more apparent. The controller 61 is connected to the positive or plus terminal of the battery 60 through a fixed contact 64 which is maintained in engaging contact when the cap member 35 is screwed into place. The controller 61 has a ring output contact 65 which is forced into engaging contact with a resilient bus bar 66 mounted on the side wall 32 of the housing 31 as the cap member 35 is screwed onto the housing side wall 32 to close same. The bus bar 66 extends along side wall 32 to engage a contact 68 on motor 50 so that power is supplied to motor 50 through the controller 61 and bus bar 66.

Figure 6:
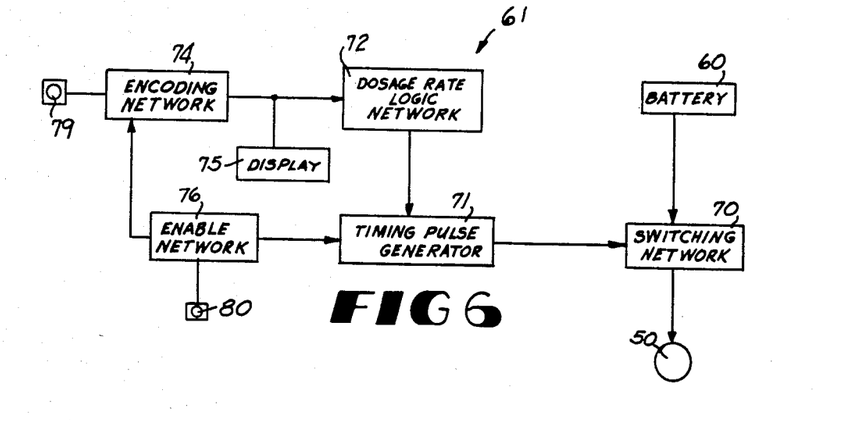
FIG. 6 is an electrical schematic of the control circuit of the driver.

The controller 61 serves to alternately connect and disconnect the battery 62 and the motor 50 so that the amount of fluid injected into the patient over a prolonged period of time can be controlled. It will be appreciated that the controller 61 may connect and disconnect the battery 60 to the motor 50 so that a fixed volume of fluid can be injected over a prescribed period of time or the controller 61 may be adjustable so that the amount of fluid injected over a prescribef period of time can be varied. Several different arrangements are disclosed in our application Ser. No. 248,512. The controller 61 schematically illustrated in FIG. 6 is of the type which can vary the volume of fluid injected over a prescribed period of time.

The controller 61 includes a switching network 70 which connects and disconnects the battery 60 to the motor 50, a timing pulse generator 71 which controls the rate at which the switching network 70 connects and disconnects the battery to the motor, a dosage rate logic network 72 which controls the pulse rate output of the timing pulse generator 71 and an encoding network 74 which allows different injection rates to be inputted into the dosage rate logic network 72 to change the rate at which the fluid is discharged from the injector. To provide a visual indication of the injection rate at which the fluid is being injected, a display 75 is connected to the output of the encoding network 74 and to prevent inadvertent change of the injection rate while the injector is operating, an enable network 76 is provided which prevents adjustment of the encoding network 74 while the injector is injecting fluid.

As best seen in the end view in FIG. 4, the display 75 has a liquid crystal readout 78 so that the injection rate is visually displayed thereon. The end of the controller 61 is further provided with a rate change switch 79 and an inject switch 80. Preferably, the switches 79 and 80 are recessed so that it is difficult to inadvertently change the setting of the injector.

The inject switch 80 is connected to the enable network 76 so that when the inject switch 80 is operated to cause the enable network to shift into the inject mode, the enable network 76 disables the encoding network 74 so that the injection rate manually inputted into the encoding network 74 cannot be changed while the timing pulse generator 71 is enabled so that the output of the timing pulse generator 71 operates the switching network 70 to cause the battery 60 to be connected and disconnected from the motor 50 at the required rate to achieve the injection rate set into the controller 61. When the switch 80 causes the enable network 76 to be in the programming mode, the enable network 76 disables the timing pulse generator 71 and enables the encoding network 74 so that the rate change switch 70 can be manually operated to operate the encoding network 74 so as to change the injection rate output therefrom the dosage rate logic network 72 and displayed on the liquid crystal readout 78 of the display 75. Preferably, the encoding netowork 74 is designed so that the injection rate set by the encoding network 74 in response to manipulation of the switch 79 increases the injection rate on alternate depressions of the switch 79 and decreases the injection rate on alternate depressions of the switch 79. Thus, the personnel setting the injection rate depresses the switch 79 to cause the rate to be shifted in one direction, such as increasing, but on alternate depression of the switch 79, the injection rate will be changed in the opposite direction, such as decreasing. Further, it is preferable that the encoding network 74 be constructed so that the longer the switch 79 is depressed, the faster the rate is changed by the encoding network 74. This allows the injection rate to be varied quickly over large rate changes, yet allows the injection rate to be accurately set at the slower speed once the injection rate has reached the vicinity of the desired rate. Thus, to set the injection rate, the personnel manipulates the switch 79 while viewing the liquid crystal readout 78 on the display 75 to determine when the desired injection rate has been reached. The dosage rate logic network 72 automatically calculates the required pulse rate to inject the desired volume of fluid in a prescribed period of time such as a 24-hour period and generates an output to the timing pulse generator 71 to cause the switching network 70 to connect and disconnect the battery to the motor 50 at the required rate to achieve the preset injection rate. The value displayed on the liquid crystal readout 78 will be the total volume of fluid which will be injected over the predetermined time period set in the dosage rate logic network 72. It will be apprciated that this pre-selected time period may be different for different applications.

An inject lamp 81 is provided on the end of the controller 61 to be periodically illuminated when the inject mode is in progress. A warning lamp 82 may also be provided to indicate some malfunction in the device such as the battery power being too low.

It will thus be seen that the plunger 30 is screwed down over the power unit 29 before it is inserted into the syringe barrel 11 as seen in FIG. 1. Preferably, the volume of fluid in the bore 21 between the piston 12 and the discharge opening 25 is selected to locate the piston 12 in the barrel 11 so that the driver 14 will engage the piston 12 as the driver 14 is installed and shift the piston 12 toward the discharge opening 25 sufficiently to flush the tubing 26 connected thereto. Thus, the need to flush at the time the driver 14 is inserted in the syringe barrell 11 is eliminated. Appropriate circuitry may also be provided to use the motor 50 to flush the tubing 26.

The volume of fluid to be injected over the prescribed period of time is then selected using the rate switch 79. When the desired volume to be injected over the prescribed period of time is displayed in the liquid crystal readout 78, the inject button 80 is depressed to shift the injector 10 into the inject mode. Each time the switching network 70 and the controller 61 connects the motor 50 to the battery 60, the motor 50 will step a prescribed amount thus rotating the drive wheel 52 through a prescribed rotational distance. This serves to likewise rotate the plunger 30 so that the plunger 30 is unscrewed a prescribed amount from the drive unit 29 and is axially shifted a prescribed distance toward the discharge opening 25 so that a prescribed volume of fluid is discharged out of the opening 25. The switching network 70 then disconnects the battery from the motor 50 and repeats the cycle at the required rate to inject the selected volume of fluid over the prescribed period of time.

Figure 7:
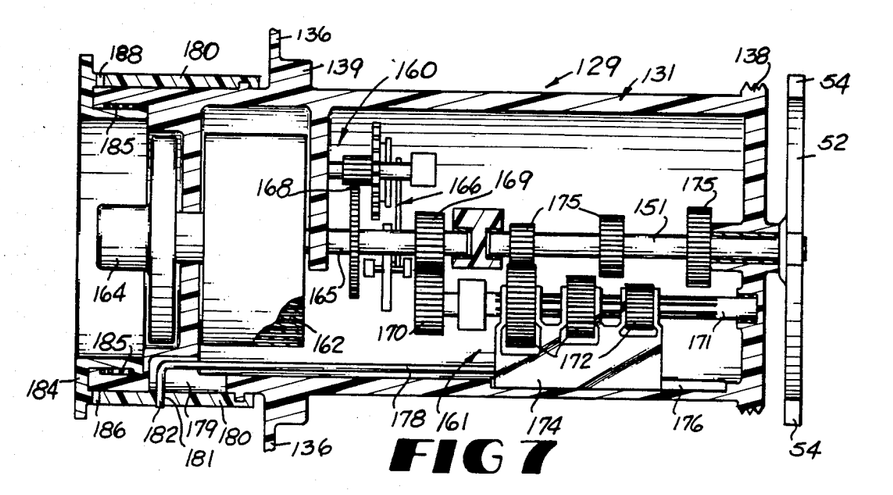
FIG. 7 is an enlarged longitudinal cross-sectional view of an alternate embodiment of the power unit of the driver of the invention.
Figure 8:
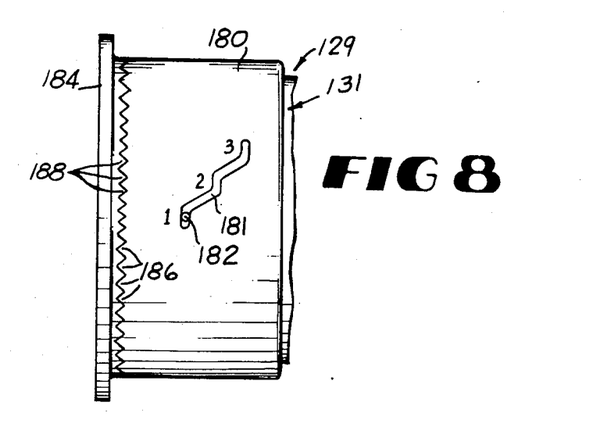
FIG. 8 is a partial elevational view of the power unit of FIG. 7.

FIGS. 7 and 8 illustrate an alternate power unit for the driver 14 which has been designated 129. The power unit 129 is spring driven rather than electrically driven as was the power unit 29. The power unit 129 is used in conjunction with the plunger 30 the same as with the power unit 29.

The power unit 129 includes an elongate cylindrical housing 131 with an outside diameter similar to the housing 31. The housing 131 has an annular side wall 132 which is closed at its leading end by the end wall 134. A pair of opposed locks 136 are partly seen mounted on the side wall 132 to engage the ears 28 on the syringe barrel 11 to lock the power unit 129 onto the syringe barrel 11. A threaded section 138 is provided around the outside of the housing side wall 132 at its leading end similar to the threaded section 38 on the power unit 29 and serves to threadedly engage the threads 44 on the plunger 30 so that the plunger 30 can be screwed down over the housing 131. A locating section 139 is provided adjacent the locks 136 to fit inside the bore 21 on the syringe barrel 11 similar to that of the power unit 29.

The power unit 129 is provided with an output drive shaft 151 coaxially located in the housing 131 and projecting out through the end wall thereof to mount the drive wheel 52 with the lugs 54 thereon. It will thus be appreciated that the lugs 54 on the drive wheel 52 engage the slots 55 in the plunger 30 similarly to the drive unit 20 and need not be described in detail. The drive shaft 151 is connected to a spring driven clockwork mechanism 160 through a transmission 161.

The clockwork mechanism 160 has a main spring 162 adapted to be manually wound with the key 164. An output shaft 165 is connected to the main spring 162 and the output rotational speed of the shaft 165 is controlled by a typical escapement mechanism 166 through its associated gear train 168. Shaft 165 mounts an output gear 169 thereon which in turn drives the transfer shaft 171. The transmission 161 has a transfer shaft 171 driven by output gear 169 through input gear 170. The transfer shaft 171 is splined and mounts a plurality of gears 172 thereon which are internally splined to match the splines on the shaft 171 so that the gears 172 can be axially shifted along the shaft 171. The gears 172 are postioned by a yoke 174 so that the gears 172 can be individually aligned with one of the output gears 175 fixedly mounted on the output drive shaft 151. It will be seen that each of the gears 172 is complementary to one of the gears 175 with the gears 172 having different diameters so that the speed ratios between the rotational speed of the transfer shaft 171 and the rotational speed of the drive shaft 151 can be changed. While there are three such gears 172 illustrated so that three speed ratios can be achieved, other arrangements can be provided without departing from the scope of the invention. The base of the yoke 174 is slidably mounted in a slot 176 in the side wall 132 to hold it in position as it slides back and forth to change the gears and a positioning rod 178 projects from one end of the yoke 174 toward that end of the housing 131 mounting the key 164. The positioning rod 178 passes out of the side wall 132 through a slot 179 therein to be engaged by a positioning ring 180 rotatably mounted on the side wall 132.

The positioning ring 180 is provided with a slot 181 therein through which the bent end 182 on the positioning rod 178 projects so that, as the positioning ring 180 is rotated around the side wall 132, the slot 179 in the side wall 132 keeps the bent end 182 of positioning rod 178 from rotating and thus causes the bent end 182 to track along the slot 181 to shift the position of the yoke 174 and thus the gears 172. The slot 181 is provided with small land sections at the position of mesh between each of the gears 172 and its corresponding gear 175 to insure good meshing between the gears. To hold the positioning ring 180 in position, a lock ring 184 is mounted in that end of side wall 132 around the key 164 so that the lock ring 180 is axially movable with respect to the side wall 132 but held rotationally fixed with respect thereto. A positioning spring 185 positioned between the side wall 132 and the lock ring 184 constantly urges the lock ring 184 toward the opposite end of the housing 132. The positioning ring 180 and the lock ring 184 are provided with complementary teeth 186 and 188 respectively so that the lock ring 184 can be pulled away from the positioning ring 180 until the teeth 188 disengage the teeth 186 on the positioning ring 180 so that the positioning ring 180 can be rotated to place the transmission 161 in the desired gear ratio setting. The lock ring 184 is then released and the spring 185 urges the teeth 188 back into mesh with teeth 186 on the positioning ring 180 to keep it in place.

The plunger 30 is screwed down over the power unit 129 similarly to that of the unit 29 and, after the desired speed is set with the positioning ring 180, the spring 162 is wound and the unit inserted into the syringe barrel 11 to inject the fluid therefrom.

Figure 9:
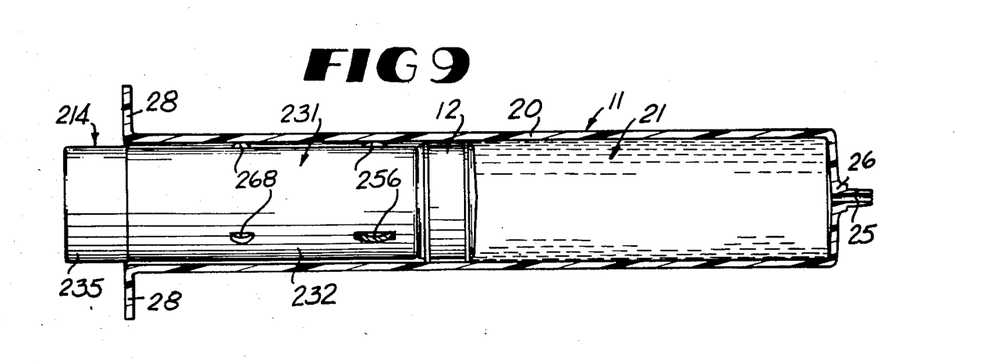
FIG. 9 is a cross-sectional view illustrating a second embodiment of the driver of the invention.

FIGS. 9–12 illustrate a second embodiment of the driver which has been designated by the numeral 214. As seen in FIG. 9, the driver 214 is inserted into the bore 21 in the syringe barrel 11 behind the piston 12 and the entire driver 214 is propelled axially along the bore 11 to eject the liquid from the syringe barrel 11.

The driver 214 includes an elongate cylindrical housing 231 with an outside diameter such that the housing 31 will be received in the bore 21 of the syringe barrel 11 in close tolerance clearance therewith. The housing 231 has an annular side wall 232 closed at its leading end by an end wall 234 to define a cavity therein opening onto the opposite end of the side wall 232. A cap member 235 threadedly engages the open end of the side wall 232 to close the cavity in the housing. When the housing 231 is pushed into the open end of the bore 21 behind the piston 12, the housing 231 can be pushed until the outside face of the end wall 234 engages the trailing end of the piston 12.

To propel the driver 214 axially along the syringe barrel 11, a driving unit 235 is provided. The driving unit 235 includes a drive motor 250 which is fixedly mounted in the cavity of housing 231 adjacent the leading end thereof so that its drive shaft 251 projects forwardly of the motor 250 into an appropriate bearing mounted in the end wall 234. Mounted on the drive shaft 251 is a helical drive gear 252 which is rotated with the shaft 251. If it is desirable to prevent the driver 214 from being inadvertently retracted out of the syringe barrel 11, a one-way clutch sprocket 254 and an associated stop dog 255 can be mounted on the shaft 251 as seen in FIG. 10.

Figures 11, 12:
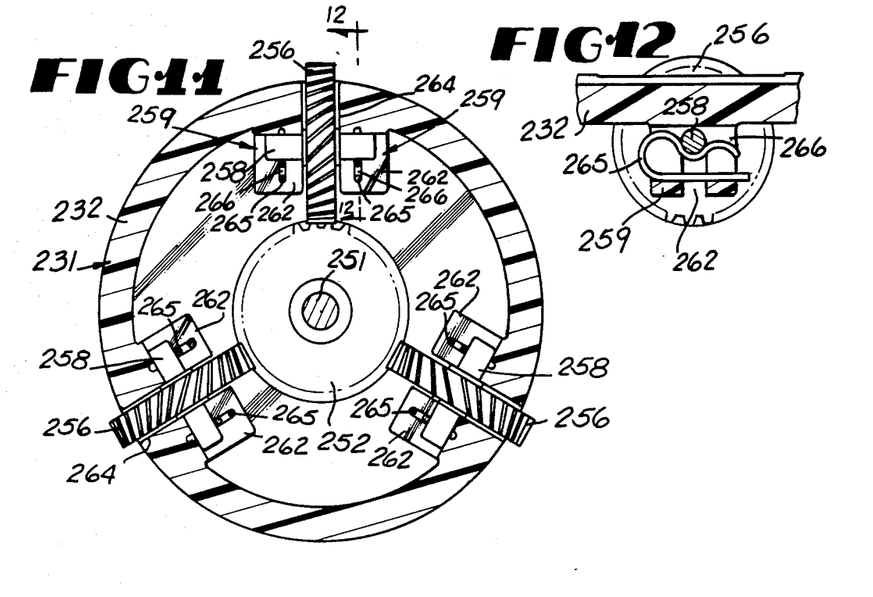
FIG. 11 is an enlarged transverse cross-sectional view taken generally along line 11—11 in FIG. 10.
FIG. 12 is an enlarged cross-sectional view taken generally along line 12—12 in FIG. 11.

Three driven helical gears 256 are rotatably mounted in the housing 231 at circumferentially spaced positions around the driven gear 252 so that the gears 256 are perpendicular to the gear 252 and each is maintained in mesh with the gear 252. Thus, as the motor 250 rotates the gear 252, all three of the driven gears 256 are rotated in the same direction. As best seen in FIGS. 11 and 12, each of the driven gears 256 has a support shaft 258 which is rotatably mounted between slotted ears 259 integral with the side wall 232 on the housing 231. The bottom of the slots 262 in the ears 259 serve to limit the outward projection of the gears 256 through the longitudinally extending slots 264 formed in the side wall 232 in registration with the gears 256. The gears 256 are urged out of the side wall 232 through the slots 264 by a pair of spring clips 265 received under the shaft 258 on opposite sides of the gear 256 in cross slots 266 through the ears 259 where the slots 266 are perpendicular to the ears 259. The resiliency of the spring clips 265 is such that the gears 256 are urged out of the housing 231 so that the diameter subtended by the gears 256 is greater than the inside diameter of the syringe barrel 11. As the gears 256 are forced into the bore 21, the side wall 20 on the barrel 11 will force the gears 256 inwardly, yet the spring clips 265 will maintain positive driving engagement between the inside surface of the side wall 20 of the syringe barrel 11 and the teeth on the gears 256. To permit this small amount of deflection of the gears 256, the meshing teeth on the gear 256 and the drive gear 252 are cut deep enough so that the gears can move toward and away from each other while still maintaining driving mesh therebetween. Thus, as the motor 250 rotates the gear 252, the gears 256 will be rotated and thus propel the driver 214 axially toward the discharge opening 25 and the syringe barrel 11 to force the piston 12 therewith and discharge the fluid from the syringe barrel 11.

It will be appreciated that the action of the spring clips 265 serve to keep the housing 231 centered with respect to the bore 21 at the leading end of the driver 214. To keep the trailing end of the housing 231 centered with respect to the bore 21, positioners 268 may be provided around the side wall 232 as seen in FIGS. 9 and 10 and spaced from the gears 256.

Figure 10:
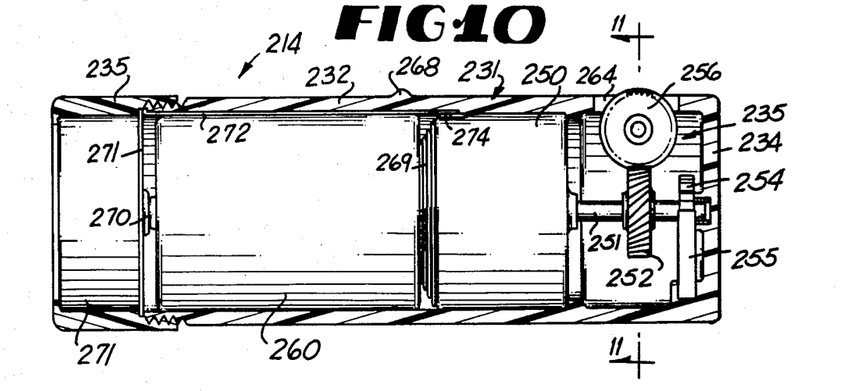
FIG. 10 is an enlarged longitudinal cross-sectional view of the driver of FIG. 9.

Battery 260 as seen in FIG. 10 is slidably mounted in the cavity of the housing 231 behind the motor 250 to power same and a controller 261 is mounted in the cap member 235 to connect and disconnect the battery 260 to the motor 250 to power same similarly to the first embodiment of the invention. Thus, it will be seen that the battery 260 is connected to the motor 250 through the conical coil spring 269 while the positive contact from the battery 260 is connected to the controller 261 through the fixed contact 270. The controller 261 is provided with a ring output contact 271 which contacts the bus bar 272 extending along the side wall 232 to engage the contact 274 on the motor 250 in a manner similar to the first embodiment of the invention. The controller 261 can have any number of constructions including the construction described in more detail with respect to the controller 61 of the first embodiment of the invention.

Thus, it will be seen that the driver 214 is pushed into the bore 21 behind piston 12 as seen in FIG. 9 and the motor 250 is stepped to incrementally rotate the gears 256 and incrementally propel the driver 214 axially along the syringe barrel 11 behind the piston 12 to discharge the fluid therefrom. Since the driver 214 will probably be totally inside the bore 21 in the syringe barrel 11 at the end of its operation, and further, since it may not be possible to pull the driver 214 back out of the syringe barrel 11, the end wall 22 on the syringe barrel 11 may be cut off on the side wall 20 and the driver 214 pushed out of that end of the syringe barrel 11 is it is desirable to reuse the driver 214.

Figure 13:
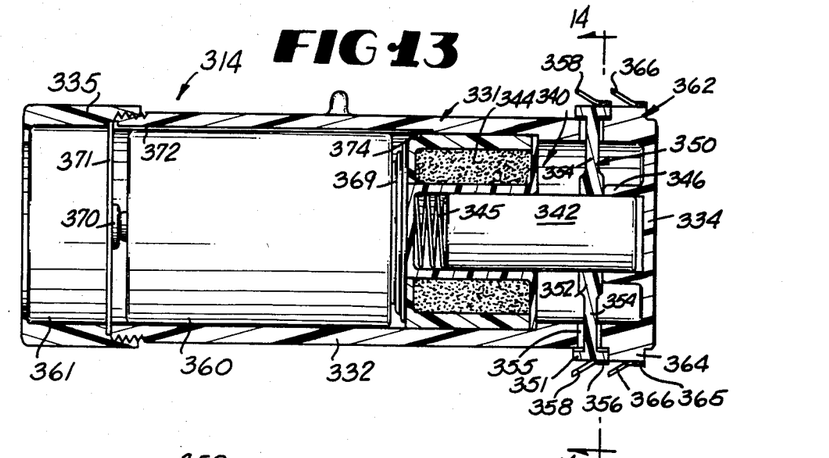
FIG. 13 is an enlarged longitudinal cross-sectional view of a third embodiment of the driver of the invention.

FIGS. 13–16 illustrate a third embodiment of the driver which is sized to pass into the bore 21 in the syringe barrel 11 in a manner similar to that described for the second embodiment of the driver. The third embodiment of the driver is designated 314 and includes an elongate cylindrical housing 331 as best seen in FIG. 13 with an outside diameter a prescribed amount smaller than the bore 21 in the syringe barrel 11. The housing 331 has an annular side wall 332 closed at its leading end by an end wall 334 to define a cavity therein opening onto the opposite end of the side wall 332. A cap member 335 threadedly engages the open end of the side wall 332 to close the cavity as will become more apparent.

To propel the driver 314 along the bore 21, a driving unit 340 is provided. The driving unit 340 includes a solenoid 341 mounted in the cavity adjacent the leading end thereof. The solenoid 341 has a plunger 342 reciprocally mounted inside the coil 344 thereof with a spring 345 that normall urges the plunger 342 out of the coil 344 while the coil 344, when energized, moves the plunger 342 into the coil 344. The plunger 342 projects from the coil 344 toward the end wall 334 and is supported in an appropriate boss 346 on the end wall 334.

Figure 14:
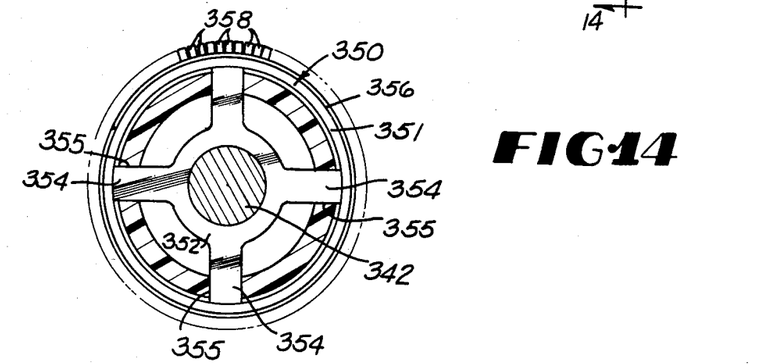
FIG. 14 is a transverse cross-sectional view taken generally along line 14—14 in FIG. 13.

Mounted on the plunger 342 and reciprocally movable therewith is a drive ring assembly 350 which has an outer ring 351 located just outboard of the side wall 332 and lying in a plane normal to the axis of the housing 331. A central web 352 is fixedly mounted on the plunger 342 and is connected to the ring 351 through radially extending spokes 354 that extend out through slots 355 in the side wall 332. The slots 355 have a circumferential width substantially equal to the width of the spokes 354 as best seen in FIG. 14 but a length greater than the thickness of the spokes 354 as best seen in FIG. 13 so that the drive ring assembly 350 can reciprocate with the plunger 342 axially of the housing 331.

Mounted on the outside of the ring 351 is a detent strip 356 with a plurality of detents 358 extending outwardly therefrom so that, when the driver 314 is pushed into the bore 21 in the syringe barrel 11, the detents 358 will be resiliently flexed to allow the drive ring assembly 350 to move toward the piston 12 in the bore 21 but the outer ends of the detents 358 will engage the inside of the side wall 20 of the syringe barrel 11 to prevent the drive ring assembly 350 from moving away from the piston 12 as will become more apparent. The drive ring assembly 350 cooperates with a holding ring assembly 362 which is fixed with respect to the housing 331.

The holding ring assembly 362 includes a raised ring 364 integral with the side wall 332 adjacent the leading end thereof and mounts thereon a detent strip 365 with outwardly angled detents 366 thereon corresponding to detent 358 on the strip 356. When the driver 314 is pushed into the bore 21 in the syringe barrel 11, the detents 366 allow the housing 331 to move toward the piston 12 but engage the inside of the side wall 20 of the syringe barrel 11 to prevent the housing 331 of the driver 314 from moving away from the piston 12. It will be appreciated that the detents 358 and 366 are resilient, and the outside diameter subtended by the detents 358 and detents 366 is slightly greater than the inside diameter of the side wall 20 on the syringe barrel 11 so that, when the driver 314 is pushed into the bore 21, the detents 358 and 366 will be deflected inwardly but their natural resiliency will constantly urge the detents out toward the side wall 20. As best seen in FIG. 14, it will be seen that a large number of detents 358 and 366 are formed in the strips 356 and 365 to insure that the detents 358 and 366 will adequately engage the side wall 20 of the syringe barrel 11 to allow the driver 314 to operate.

Figure 15:
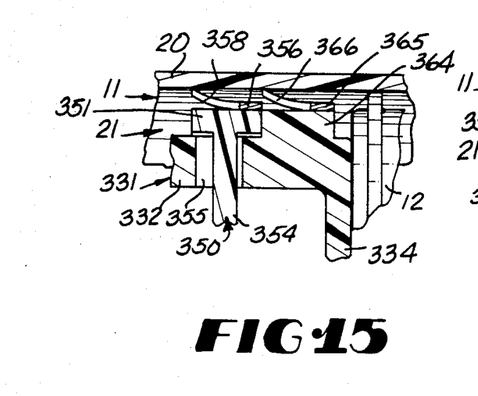
FIGS. 15 and 16 are enlarged portions of FIG. 13 illustrating the operation of the third embodiment of the driver of the invention.
Figure 16:
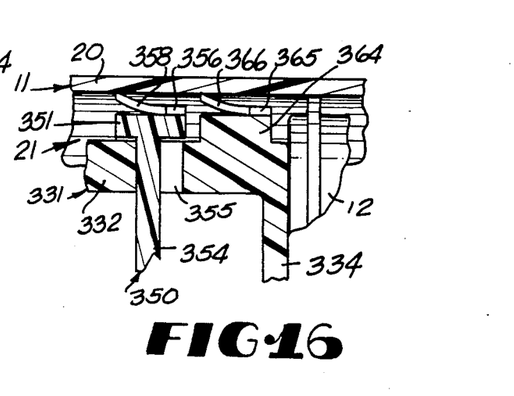

As best seen in FIGS. 15 and 16, the drive ring assembly 350 serves to incrementally advance the driver 314 axially along the bore 21 while the holding ring assembly 362 serves to keep the driver 314 in place while the drive ring assembly 350 is reset for another advancement of the driver 314. FIGS. 13 and 15 show the position of the drive ring assembly 350 while the solenoid 341 is deenergized. In this position, it will be seen that the spring 345 urges the ring 351 forwardly until it abuts the trailing edge of the ring 364 of the holding ring assembly 362. When the coil 344 in solenoid 341 is energized, it tries to pull the plunger 342 into the coil 344 against the spring 345. Since the detents 358 are engaging the inside of the side wall 20 on the syringe barrel 11, movement of the drive ring assembly 350 away from the piston 12 is prevented. This causes the plunger 342 to remain stationary while the coil 344 advances over the plunger 342 carrying with it the housing 331 since the detents 366 on the holding ring assembly 362 permit the housing 361 to move toward the piston 12. Thus, the energizing of the coil 344 advances the housing 331 and thus the piston 12 to discharge fluid out of the syringe barrel 11. The length of the stroke each time the solenoid 341 is energized is illustrated as being controlled by the length of the slots 355 in the housing side wall 332; however, appropriate adjustments can be made to allow the length of the stroke to be preset. The position of the drive ring assembly 350 ast the end of its advancement stroke is illustrated in FIG. 16.

When the solenoid 341 is deenergized, the spring 345 urges the plunger 342 out of the coil 344. Since the detents 366 prevent the housing 331 from moving away from the piston 12, the housing 331 will be held in position by the detents 366 and the drive ring assembly 350 will advance toward the holding ring assembly 362 back to the original position as seen in FIG. 15. This completes the cyle of operation which can be repeated as required to advance the driver 314 along the bore 21 in the syringe barrel 11.

Battery 360 as seen in FIG. 13 is slidably mounted in the cavity of the housing 331 behind the solenoid 341 to power same and a controller 361 is mounted in the cap member 335 to connect and disconnect the battery 360 to the solenoid 341 to power same. Thus, it will be seen that the battery 360 is connected to the solenoid 341 through the conical coil spring 369 while the positive contact from the battery 360 is connected to the controller 361 through the fixed contact 370. The controller 361 is provided with a ring output contact 371 which contacts the bus bar 372 extending along the side wall 332 to engage the contact 374 on the solenoid 341 in a manner similar to the first embodiment of the invention. The controller 361 can have any number of constructions including the construction described in more detail with respect to the controller 61 of the first embodiment of the invention.

Thus, it will be seen that the driver 314 is pushed into the bore 21 behind piston 12 similarly to the driver 214 as seen in FIG. 9 and the solenoid 341 is cyled to incrementally propel the driver 314 axially along the syringe barrel 11 behind the piston 12 to discharge the fluid therefrom. Since the driver 314 will probably be totally inside the bore 21 in the syringe barrel 11 at the end of its operation, and further since it is not possible to pull the driver 314 back out of the syringe barrel 11, the end wall 22 on the syringe barrel 11 may be cut off of the side wall 20 and the driver 314 pushed out of that end of the syringe barrel 11 if it is desirable to reuse the driver 314.

Figure 17:
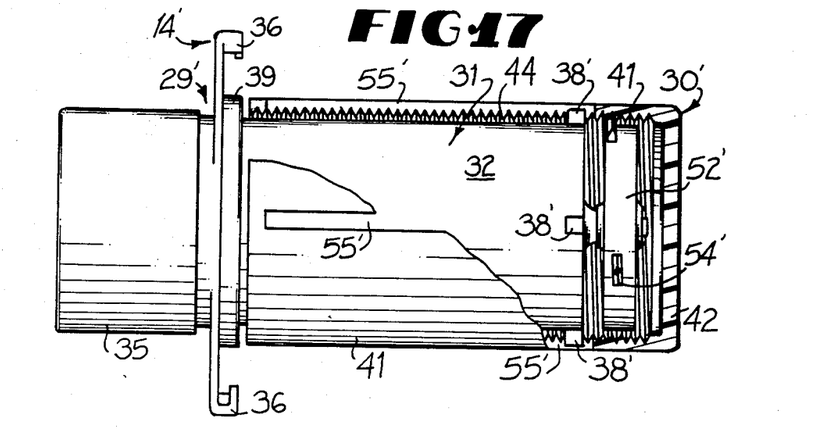
Figure 18:
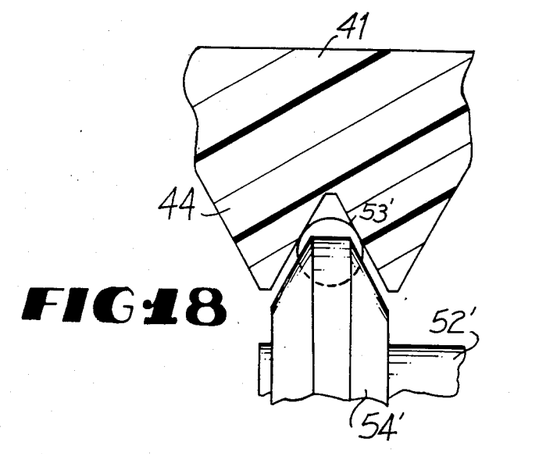

FIGS. 17 and 18 disclose an alternate driver 14' where the driving connection between the power unit 29' and plunger 30' is reversed from that of driver 14 as will become more apparent. This allows the plunger 30' to advance along the bore 21 in the syringe barrel 11 without rotating with respect thereto. Those portions of the power unit 29' and the plunger 30' which are common to the power unit 29 and plunger 30 have the same reference numbers applied thereto.

The housing side wall 32 is provided with locating lugs 38' spaced around the outside of the leading end thereof in lieu of the threaded section 38 on the power unit 29. The lugs 38' engage slots 55' in the plunger side wall 41 to keep the plunger 30' from rotating with respect to the power unit 29' yet permit relative axial movement between the power unit 29' and plunger 30'. The drive wheel 52' is provided with tooth segments 54' which drivingly engage the internal threads 44 in plunger 30' to advance the plunger 30' axially of the power unit 29' as the drive wheel 52' is rotated. To minimize friction, the tooth segments 54' may be provided with bearings 53' as best seen in FIG. 18 to provide the point of contact between the threads 44 and each tooth segment 54'.

It will further be appreciated that the motor 50 in the power unit 29' may be used to drive a threaded shaft connected to the plunger 30' and extending axially through motor 50 to advance the plunger 30'. This threaded shaft would be used in lieu of the drive wheel 52' and internal threads 44. The battery arrangement would also be reordered to accommodate the threaded shaft.

The drivers 14 and 14' initially extend into the syringe barrel 11 for about one-half its length. This serves to minimize the overall length of the injector while at the same time keeping the moving parts thereof within the barrel 11 at all times.

What is claimed as invention is:

1. A syringe injector for injecting liquids into patients comprising:
   a syringe barrel defining a cylindrical bore therein opening onto one end thereof and a discharge opening in the other end thereof communicating with said bore;

a piston slidably mounted in said bore and in sealing engagement with said barrel for movement toward said discharge opening to force liquid in said bore between said piston and said discharge opening out through said discharge opening; and a driver slidably extending into said barrel bore from the open end thereof behind said piston, said driver including:

a housing having a projecting end and a trailing end, said housing defining external threads therearound at the projecting end thereof;

an internally threaded tubular plunger screwed onto the external threads on said housing and extending over said housing so that, when said driver extends into said barrel bore with the projecting end of said housing facing said piston, said plunger engages said piston and moves said piston toward said discharge opening as said plunger is unscrewed from over said housing;

locking means adjacent the trailing end of said housing to selectively engage said barrel and fix said housing axially of said barrel bore;

a power supply; and drive means operated by said power supply, said drive means including a drive shaft projecting from the projecting end of said housing and oriented coaxially of said plunger and a drive wheel mounted on said drive shaft adjacent the projecting end of said housing for rotation with said drive shaft, said drive wheel including at least one drive lug thereon and said plunger defining at least one longitudinally extending slot therein into which said drive lug projects so that, when said drive means rotates said drive shaft and said drive wheel, said drive lug rotates said plunger to unscrew said plunger from over said housing to cause said plunger to move relative to said barrel to engage and propel said piston toward said discharge opening.

2. The syringe injector of claim 1 wherein said drive means further includes an electric motor rotating said drive shaft and wherein said power supply includes a battery electrically connected to said motor to operate same.

* * * * *